United States Patent [19]

Diana et al.

[11] Patent Number: 4,761,505

[45] Date of Patent: Aug. 2, 1988

[54] PROCESS FOR RECOVERY OF ALCOHOLS FROM SULFURIC ACID STREAMS

[75] Inventors: William D. Diana, Belle Mead; Chuen Y. Yeh, Edison, both of N.J.

[73] Assignee: Exxon Research & Engineering Co., Florham Park, N.J.

[21] Appl. No.: 888,581

[22] Filed: Jul. 21, 1986

Related U.S. Application Data

[63] Continuation of Ser. No. 776,387, Sep. 16, 1985, abandoned.

[51] Int. Cl.⁴ .................. C07C 29/86; C07C 31/12
[52] U.S. Cl. .................................. 568/918; 260/419; 260/429.5; 568/886; 568/888; 568/889; 568/890
[58] Field of Search ............... 568/918, 886, 888–890

[56] References Cited

U.S. PATENT DOCUMENTS

| | | | |
|---|---|---|---|
| 1,954,506 | 4/1934 | van Peski et al. | 568/889 |
| 2,081,721 | 5/1937 | van Dijck et al. | 568/918 |
| 2,109,462 | 3/1938 | Burk et al. | 568/888 |
| 2,196,177 | 4/1940 | Burk et al. | 568/918 |
| 2,510,806 | 6/1950 | Egbert et al. | 568/918 |
| 2,535,069 | 12/1950 | Johnson | 568/918 |
| 3,489,779 | 1/1970 | Bearden | 260/419 |
| 3,527,790 | 9/1970 | Moundlic et al. | 568/889 |

FOREIGN PATENT DOCUMENTS

| | | | |
|---|---|---|---|
| 334228 | 9/1930 | United Kingdom | 568/889 |
| 411303 | 6/1934 | United Kingdom | 568/889 |
| 830369 | 3/1960 | United Kingdom | 568/889 |

OTHER PUBLICATIONS

Munson et al, *Ind. Eng. Chem. Proc. Des. Dev.*, vol. 23, No. 1, pp. 109–115 (1984).

Primary Examiner—J. E. Evans
Attorney, Agent, or Firm—J. B. Murray, Jr.; D. E. Furman

[57] ABSTRACT

According to the process of the present invention, carboxylic acids are recovered from aqueous strong acid mixtures thereof which mixtures are formed as an alcohol-depleted phase by the extraction of alcohols from aqueous strong acid solution with carboxylic acids, by contacting the mixtures with a liquid organic solvent, to form a purified aqueous strong acid stream depleted in such carboxylic acid by contacting such aqueous strong acid mixtures with a liquid organic solvent, such as an alkane, alkene or di-alkyl ether to form a purified aqueous strong acid depleted in such carboxylic acid.

17 Claims, 2 Drawing Sheets

PROCESS FOR RECOVERY OF ALCOHOLS FROM SULFURIC ACID STREAMS

This is a continuation of application Ser. No. 776,387, filed 9/16/85, now abandoned.

CROSS-REFERENCE TO RELATED APPLICATIONS

This application is related to co-pending application U.S. Ser. Nos. 650,874, now U.S. Pat. No. 4,538,010 filed Sept. 17, 1984, and 650,875, filed Sept. 17, 1984, now abandoned.

BACKGROUND OF THE INVENTION

1. Field of the Invention

This invention relates generally to the recovery of alcohols from concentrated aqueous acid streams.

2. Description of the Prior Art

Large volumes of alcohols are produced annually by the catalytic hydration of olefins, in which the selected olefin feed is absorbed in a concentrated aqueous sulfuric acid stream to form the corresponding alcohol and alkyl ester of the sulfuric acid. For example, the absorption of butene to form sec-butanol and a sec-butyl ester of sulfuric acid can be illustrated by the following equation:

Thereafter, water is admixed with the sulfuric acid stream withdrawn from the absorber to hydrolyze the ester and to facilitate alcohol recovery which is accomplished by stripping with steam. There is thereby produced a diluted sulfuric acid stream which must for economic reasons be treated to concentrate it with respect to its sulfuric acid content, after which it is recycled to the olefin absorption step.

The reconcentration of the diluted sulfuric acid stream is a very expensive and energy-intensive process step, and a method whereby the alcohol could be recovered from the sulfuric acid stream withdrawn from the absorber, which did not require such a reconcentration, would be highly desirable.

Processes have been proposed for alcohol recovery by extraction from such alcohol-containing sulfuric acid streams by use of benzene, chloroform, ether, carbon bisulfide and toluene (U.S. Pat. No. 1,365,046); phenols, cresols, their homologues, ethers and phosphates (U.S. Pat. No. 2,139,953); and saturated hydrocarbons (British Pat. No. 493,884). British Pat. No. 506,473 relates to a method for production of organic oxy-compounds from a mixture of two liquid phases containing the oxy-compound distributed between the two layers in which the layers are separated and then recontacted at a lower temperature to extract the oxy-compound from the more hydrophobic phase, e.g., a hydrocarbon phase.

However, such extraction methods are not commercially desirable, since the solvents extract very little alcohol if the acid strength of the alcohol-containing sulfuric acid stream is greater than about 55%. Dilution of the acid stream to improve the ability of these solvents to extract the alcohol is not economically practicable, since even more expense would be incurred in reconcentrating the resulting sulfuric acid (recovered after the extraction) prior to its being recycled to the olefin absorbing step.

C. L. Munson et al., Ind. Eng. Chem. Proc. Des. Dev., vol. 23, no. 1, pp. 109–115 (1984) (which is not admitted herein to be prior art) investigated equilibrium distribution coefficients and separation factors for extraction of ethanol from dilute aqueous solutions of the alcohol by a number of different solvents and solvent mixtures, including extraction solvents comprising neodecanoic acid and 2-ethyl hexanoic acid. An ethanol-water-extraction solvent phase is obtained and treated to dehydrate the ethanol, followed by fractionating the ethanol and solvent mixture. The dilute aqueous raffinate is separated from the extractor and treated, as by stripping, to separate extraction solvent dissolved in the raffinate.

U.S. Pat. No. 3,489,779 to Esso Research and Engineering Company is directed to a process for purifying neo-carboxylic acids by treating the neo acid with concentrated sulfuric acid (85+ wt. % $H_2SO_4$) followed by treatment with a phase-separating agent, which can either comprise water or a paraffinic hydrocarbon. The function of the concentrated sulfuric acid is to convert olefinic and other impurities (e.g., Fe) into the corresponding sulfates. If water is added as the phase-separating agent it must be used in carefully controlled amounts, sufficient to liberate the neo-acid from its sulfuric acid complex but insufficient to hydrolyze the alkyl sulfates and other impurities formed in the first step. A water and neo-acid mixture, containing a lessened impurity level, is recovered. When a paraffinic hydrocarbon is used, a paraffin and neo-acid mixture is recovered as a separate liquid phase, and the sulfate impurities remain in the sulfuric acid phase. In the latter process alternative, the separated paraffin/neo-acid layer still contains 5–10 wt. % $H_2SO_4$ which must be removed.

SUMMARY OF THE INVENTION

According to the process of the present invention, alcohols are recovered from aqueous mixtures thereof with a concentrated strong acid by (a) contacting such alcohol-containing aqueous concentrated acid mixtures with a carboxylic acid extractant selected from the group consisting of acids of the formula $RCO_2H$ wherein R is a straight or branched-chain or cyclic alkyl of from 5 to 19 carbon atoms per molecule to form an extract phase containing the carboxylic acid in addition to the alcohol, and an aqueous raffinate phase depleted in the alcohol and containing entrained extractant, (b) recovering the alcohol from the extract phase, and (c) contacting the aqueous raffinate phase with a organic extractive agent to separate at least a majority of the entrained carboxylic acid extraction solvent therefrom.

As disclosed in Ser. No. 650,875, filed Sept. 17, 1984 (the disclosure of which is hereby incorporated by reference), it has been surprisingly found that the above extraction solvents efficiently remove alcohol from concentrated aqueous strong acid solutions thereof and permit recovery of this alcohol without substantial dilution of the aqueous strong acid. The extraction solvents of this invention permit only minor amounts of water to pass into the extraction solvent phase so that alcohol can be recovered substantially free of water. However, the recovered strong aqueous acid raffinate, depleted in alcohol, has been unexpectedly found to contain (entrained and/or solubilized therein) small amounts of the carboxylic acid extraction solvent. The present inventors have discovered that the carboxylic acid extraction solvent can be quickly and economically separated from such raffinates by contacting the raffinate with a organic extractive agent. The carboxylic acid partitions efficiently into the organic extractive agent and permits a strong acid raffinate, freed of substantial contamination by the carboxylic acid, to be recovered. The thus treated strong acid raffinate can then be readily recycled, for example, directly to an olefin absorption process for absorption of additional olefin.

DETAILED DESCRIPTION OF THE INVENTION

Prior Art Methods

Figure 1:
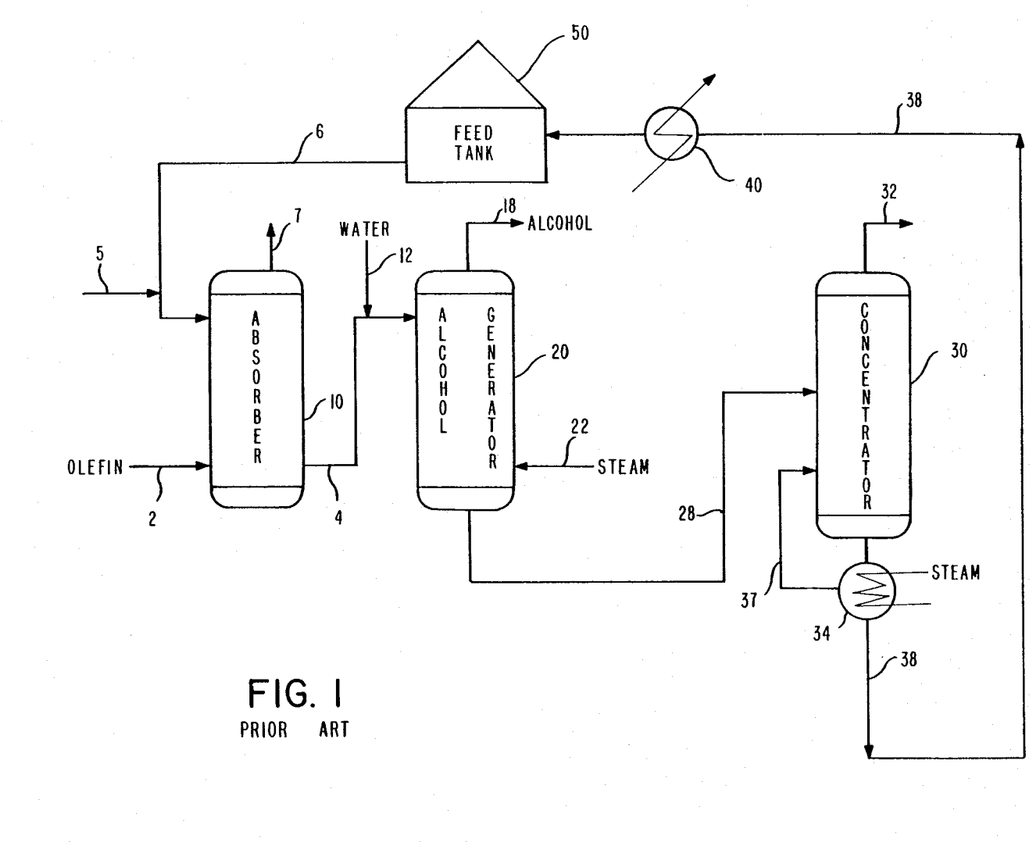
FIG. 1 is a diagrammatic illustration of a prior art process for indirect hydration of olefins using sulfuric acid, dilution of the sulfuric acid extract and stream stripping of the diluted acid for recovery of the alcohol vapors.

The prior art method of producing alcohols by hydrating the corresponding olefin can be illustrated by reference to FIG. 1. An olefin, for example an aliphatic olefin having from 2 to 8, and more typically from 2 to 4, carbon atoms per molecule (e.g., ethylene, propylene, or 1- or 2-butene) is fed as a gas or liquid via line 2 to an absorber 10 wherein it is contacted with and absorbed (at least in part) by a concentrated aqueous strong acid stream introduced via line 6, to form the corresponding alcohol and alkyl ester of the strong acid.

The olefins to be hydrated can be obtained from any available source, such as the destructive distillation of carbonaceous materials, but particularly from the cracking of petroleum hydrocarbons such as is practiced in the petroleum refining of mineral oils. The olefin can also be conventionally obtained by careful fractionation of cracked petroleum gases and is preferably substantially free of higher unsaturates, particularly diolefins such as butadiene, etc. Illustrative of olefins which are employed are lower branched and straight-chain alkenes (i.e., alkenes of 2 to 6 carbon atoms), such as ethylene, propylene, the butylenes and the like.

The strong acid used to absorb the olefin in absorber 10 (also termed "olefin hydration acid") will generally comprise a strong organic or inorganic acid which is miscible with water and which is characterized by dissociation constants ("pK" values) in aqueous solutions of less than about 3.5. Examples of suitable inorganic olefin hydration acids are hydrofluoric acid, hydroiodic acid, hydrochloric acid, ortho-phosphoric acid, phosphorous acid, perchloric acid, sulfuric acid and the like. Sulfuric acid is especially preferred. Examples of suitable organic olefin hydration acids are chloroacetic acid, benzene sulfonic acid and the like. For convenience, the following discussion will be directed to the use of sulfuric acid, although it will be understood that any of the above strong acids could also be employed.

The aqueous strong acid stream 6 which is used to absorb the selected olefin feed is a concentrated acid stream whose precise acid concentration will vary depending on the olefin which is employed, the strong acid selected, the temperatures of reaction and other conditions. For example, when sulfuric acid is used as the strong acid, stream 6 will generally contain from about 45 to 99% acid strength sulfuric acid for hydration of propylene and from about 55 to 85% acid strength sulfuric acid for reaction with butylene or higher olefin feeds.

The temperature and pressure employed in absorber 10 generally also varies depending on the olefin, the acid concentration and other factors. Generally, a temperature of from about 20° to 150° C. is used, and the pressure is sufficient to maintain the desired liquid phases in the absorber. Typically, for example, propylene is absorbed from a gas phase at a temperature of from about 90° to 150° C., and at a pressure of from about 100–500 psig.

As illustrated, the olefin and sulfuric acid streams are contacted in a counter-current fashion with the sulfuric acid stream being introduced into the upper portion of the absorber 10. Unabsorbed gases are withdrawn from the upper portion of absorber 10 via conduit 7 and can be recycled, if desired, to conduit 2 or can be subjected to conventional scrubbing/washing treatment, as with caustic solutions. A product stream, comprising a sulfuric acid solution of the alcohol (herein termed the "absorber product stream"), is withdrawn via line 4 from the lower portion of absorber 10. The absorber product stream can also contain the alkyl ester corresponding to the selected olefin, e.g., monoethyl sulfate when ethylene is the olefin, and mono-isopropyl sulfate in the case of propylene hydration. The concentration of the alkyl ester in stream 4 can vary widely, and is generally from 15 to 30 wt. % of the total alkyl ester (mono- and di-alkyl ester) in the case of lower alkenes (e.g., propylene and butylene) absorption.

In the second step of the hydration process, water is conventionally added via line 12 to the absorber product stream 4 for hydrolysis of any alkyl ester and to form additional quantities of the corresponding alcohol, e.g., isopropanol from mono- or di-(isopropyl) sulfate. The manner in which the water and absorber product stream are contacted varies, and the art employs a variety of such methods, including (1) in-line addition of water (as illustrated), with a provision for a suitable length of conduit to provide adequate mixing and reaction time, and (2) contacting of the absorber product stream and water in a separate reaction vessel with agitation (not shown).

The amount of water which is added to the absorber product stream also varies widely. Generally, sufficient water is added in order to reduce the acid strength to from 45% to 55% sulfuric acid. These reduced acid strengths are desired to permit subsequent recovery of the alcohol by steam stripping. Typically, from about 0.2 to 0.5 parts by weight of water is added per part by weight of the absorber product stream.

The diluted stream thus formed generally contains from about 45 to 55 wt. % sulfuric acid, and is then passed via line 4 to distillation column 20, herein termed the "alcohol generator," wherein crude alcohol is recovered as an overhead product via line 18 by steam stripping. The overhead alcohol product can then be passed to further conventional processing to produce alcohol of the required purity.

A bottoms product is withdrawn from alcohol generator 20 via line 28 and comprises a sulfuric acid stream which generally contains from about 40 to 55 wt. % sulfuric acid.

In conventional processes, the alcohol generator bottoms 28 are passed directly to another distillation column 30, hereinafter term the "acid concentrator", wherein this acid stream is distilled (e.g., by use of a steam heat exchanger 34 and reboiled stream 37 for removal of water as overhead 32 and to form a second bottoms product 38 comprising a reconcentrated acid stream. These concentrated bottoms are generally cooled in cooler 40 and passed to storage tank 50 for ultimate recycle to the absorption step 10, with addition of make-up acid 5, as required.

Present Invention

Figure 2:
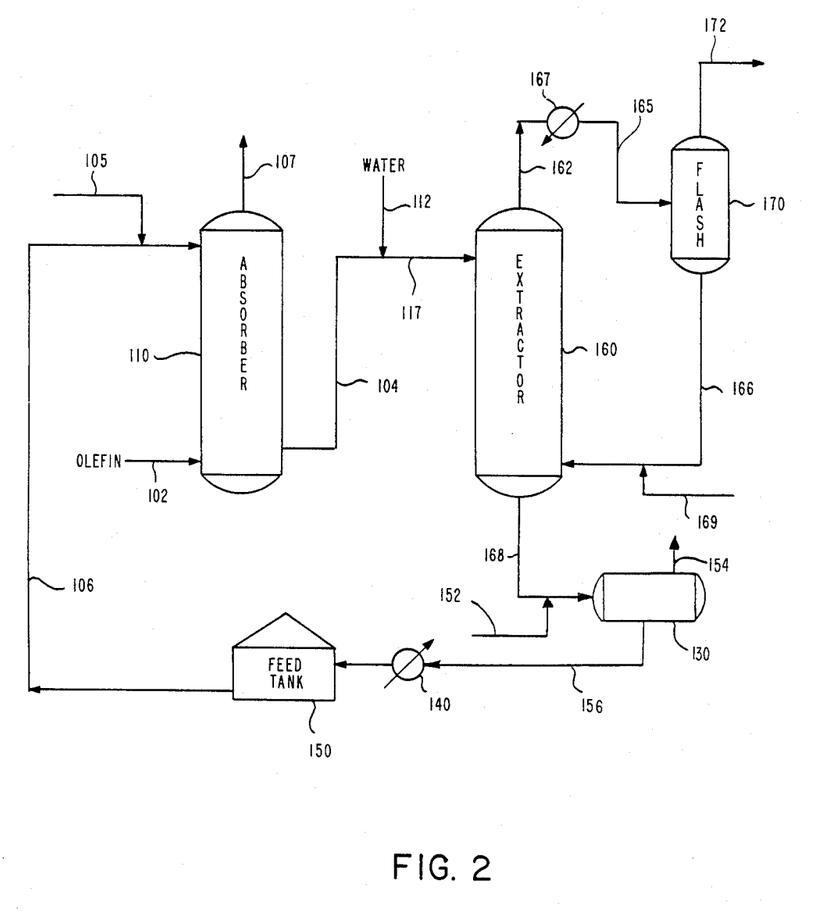
FIG. 2 is a diagrammatic illustration of one embodiment of the process of this invention.

Referring to FIG. 2, a concentrated aqueous strong acid alcohol-containing solution 104 (herein termed the "acid/alcohol feedstream" is contacted with an effective amount of an extraction solvent 166 selected from the group consisting of alicyclic and acyclic alkyl carboxylic acids having from 6 to 20 carbon atoms per molecule. The carboxylic acids which are employed as extraction solvents 166 in the process of this invention therefore comprise at least one member selected from the group consisting of carboxylic acids of the formula:

wherein R is an alicyclic or acyclic alkyl group having from 5 to 19 carbon atoms. When "R" is acyclic alkyl, the alkyl group can be straight or branched chain. The "R" group can be substituted with nonreactive groups such as fluoro and chloro. Examples of such "R" groups are pentyl, hexyl, decyl, dodecyl, tetradecyl, undecyl, 2-ethylhexyl, cyclohexyl, cyclooctyl and fluoro- and chloro- substituted derivatives of the foregoing.

A preferred class of carboxylic acid extraction solvents for use in this invention comprise saturated acids, and especially saturated hindered acids wherein the carboxyl groups are sterically blocked or hindered. The discussion of steric hindrance may be found in Newman, Steric Effects in Organic Chemistry, 1956, pp. 204–207. Generally, steric hindrance results from the presence of tertiary or quaternary alpha, beta or gamma carbon atoms in the acid, increasing substitution leading to increased hindrance. Steric hindrance has been observed to tend to prevent esterification of the carboxylic acid with the alcohol.

A class of particularly preferred sterically hindered carboxylic acids are the neo acids ("neo" is used to denote a carbon atom that is bonded to four other carbon atoms, e.g., as in neo-hexanoic acid, i.e., 2,2-dimethyl butanoic acid). Thus, the preferred neo-acids can be represented by members selected from the group consisting of acids having the formula (II):

wherein $R^1$, $R^2$ and $R^3$ are the same or different and are independently selected from the group consisting of cyclic and alicyclic alkyl of from 1 to 16 carbon atoms, with the proviso that the neo acid contains a total of from 6 to 20 carbon atoms per molecule, and preferably from 7 to 15 carbon atoms per molecule. The alicyclic alkyl groups can be straight or branched. A preferred class of neo acids are those wherein, referring to formula II above, $R^1$ and $R^2$ are preferably each alkyl radicals having from 1 to 3 carbon atoms per radical and $R^3$ is preferably alkyl having from 1 to 6 carbon atoms, provided that the neo-acid has a total of at least 6, and preferably at least 7, carbon atoms per molecule.

Some typical examples of neo acids are 2,2-dimethyl butanoic acid; alpha, alpha-dimethyl cyclohexyl acetic acid; alpha,alpha-dimethyl octanoic acid; 1-methyl-4-propylcyclohexane-1-carboxylic acid; and the like.

Commercial neo-acids which comprise a mixture of isomers, all with the neo structure (formula II), such as neo-heptanoic acid, neo-octanoic acid, neononanoic acid, neo-decanoic acid and neo-tridecanoic acid, are especially useful and preferred in the process of this invention. The preparation and properties of the commercial carboxylic acids are described in N. Fefer and A. Rutkouski, J. Am. Oil Chemists' Soc., 45, 5 (1968). Neo acids can also be prepared by the well-known Koch process from carbon monoxide, water and type II, III, IV or V olefins as described by H. Koch in Brenntstaff Chem., 36, 321 (1955). Further details on methods for making neo acids can be found in British Pat. No. 998,974 and U.S. Pat. No. 3,349,107, all of which are hereby incorporated by reference. Neo acids are often made from branched chain olefin feedstocks which are random isomeric mixtures in regard to the position of the olefinic bond. These acids are thus random isomeric mixtures of neo acids. These neo acids are suitable in their isomeric forms, or any suitable mixtures thereof may be employed.

The carboxylic acid extraction solvent may be used alone or as mixtures with a cosolvent for the selected alcohol, such as a $C_{10}$ to $C_{20}$ paraffinic hydrocarbon, a $C_7$ to $C_{12}$ aromatic hydrocarbon, or a $C_1$ to $C_{10}$ alkyl ester of a $C_4$ to $C_{15}$ monocarboxyic acid. When used, such additional cosolvents will be generally employed in such mixtures in an amount of less than about 70 wt. % (and preferably less than 50 wt. %) of the carboxylic acid/cosolvent mixture. In particular, it has been observed that the carboxylic acid extraction solvents of this invention, when contacted with alcohol and concentrated aqueous acid, will form the corresponding carboxylic ester of the alcohol, albeit at a rate which varies depending on the particular carboxylic acid extraction solvent selected for use. For example, steric hindrance in the carboxylic acid, especially the neo structures (Structure II) will tend to reduce the rate and equilibrium constant of the esterification reaction. Eventually, the thus-formed ester of the carboxyic acid extraction solvent will build up to approximately a steady-state concentration in the continuous process in which the carboxylic acid extraction solvent is repeatedly recycled to extract additional quantities of alcohol from the alcohol-containing concentrated aqueous acid feedstream (as will be described in more detail below).

The selected carboxylic acid extraction solvent of this invention may be contacted with the acid/alcohol feedstream in extraction zone 160 in any convenient manner, including continuous, semi-continuous or batchwise operations, in a single or in multiple extraction stages. The concentration of the strong acid (e.g., sulfuric acid) in acid/alcohol feedstreams 104 (herein termed the "acid strength" or "A.S.") to be so contacted, can vary widely and will typically range from about 40 to 80 wt. % sulfuric acid, preferably from about 50 to 65 wt. % sulfuric acid when a neo acid is employed as the extracting solvent. As used herein, the acid strength in the acid/alcohol feedstream is defined herein on an organic free basis, as follows (using H₂SO₄ as the acid for purposes of illustration).

$$A.S. = \frac{W_1 + \left[\frac{M_1 \times W_4}{M_1 + M_5}\right]}{W_1 + W_2 + \left[\frac{18 W_3}{M_3}\right] + \left[\frac{M_1 \times W_4}{M_1 + M_5}\right]} \times 100$$

wherein $W_1$ is the weight of the strong acid, $W_2$ is the weight of $H_2O$, $W_3$ is the weight of alcohol, $W_4$ is the weight of the mono alkyl ester of the strong acid, $M_3$ is the molecular weight of the alcohol, $M_1$ is the molecular weight of the strong acid, and $M_5$ is the molecular weight of the olefin. Also, the concentrations of the alcohol and alkyl ester in the stream 104 can vary widely, and the saturated monoalcohol concentration will generally range from about 5 to 50 wt. % and preferably from 10 to 40 wt. % and the saturated alcohol alkyl ester of the strong acid will generally range from about 1 to 15 wt. %, and preferably from about 1 to 5 wt. %, of total alkyl ester (mono- and di-alkyl ester).

The amount of carboxylic acid extraction solvent which is used to contact the acid/alcohol feedstream can also vary widely. Preferably, the carboxylic acid extraction solvent and the acid/alcohol feedstream are contacted in zone 160 in a ratio of from about 0.3 to 5 parts by weight of the carboxylic acid per part by weight of the acid/alcohol feedstream.

The temperature and pressure in zone 160 in which such extraction is performed using the carboxylic acid solvents of this invention is not critical, and will vary widely depending upon the particular carboxylic acid solvent employed, the degree of efficiency or removal desired for the alcohol, phase settling time desired, and other factors. Generally, however, temperatures within the range from about 25° to 100° C., preferably from about 25° to 80° C., can be used, and the pressure can be atmospheric, subatmospheric or superatmospheric, with pressures of from about 2 to 100 psig being typically suitable. Similarly, the time for the contacting of the selected carboxylic acid solvent and the acid/alcohol feedstream is not critical and can vary widely, but will typically fall within the range of from about 0.1 to 6 hours.

Finally, the process of this invention can employ as extraction zone 160, in which the extraction with carboxylic acid solvent is carried out, any of the conventional equipment which are employed for liquid-liquid extractions. For example, the solvent and the acid/alcohol feedstream can be introduced as a combined stream into a stirred tank, and the resulting liquids passed to a settling drum from which the light phase (alcohol solvent phase) and the heavy phase (lean acid-/alcohol phase) can be recovered. Alternatively, the contacting zone can comprise a static plate extraction column (either packed or trayed column), a reciprocating plate column (such as the KARR ® column), stirred columns (such as YORK-SCHIEBEL ® columns) and the like.

In the process of this invention, water may be added to the acid/alcohol feedstream 104 in order to provide the water of hydration for formation of the selected alcohol from alkyl ester corresponding to the alcohol. This water can be introduced via stream 112 into the conduit carrying the acid/alcohol feedstream 104 as illustrated, or the water can be introduced into zone 160 itself. Generally, from about 0.04 to 0.4 parts by weight of water are added per part by weight of the acid/alcohol feedstream.

An alcohol-rich carboxylic acid extract stream 162 can be thus separated and recovered as the light phase from extraction zone 160, either directly from zone 160 (as illustrated) or following treatment of a two-phase mixture removed from the contacting zone to a conventional phase separation vessel. This alcohol-rich carboxylic extract 162 generally contains from about 5 to 20 wt. % alcohol and from about 95 to 45 wt. % of the carboxylic acid solvent. The alcohol-rich carboxylic acid extract 162 will only contain a minor proportion of water, preferably less than about 2 wt. % water, more preferably less than about 1 wt. % water, and most preferably less than about 0.3 wt. % water. In addition, it has been found that the carboxylic acid extraction solvents of this invention permit recovery of such an alcohol-rich stream without, at the same time, contamination with significant amounts of the strong acid or alkyl ester of the strong acid. Generally, the alcohol-rich carboxylic acid extract 162 recovered from the contacting zone contains less than about 1 wt. %, most preferably less than about 0.3 wt. %, of such alkyl esters and is substantially free of the strong acid, that is, contains less than 0.1 wt. % and most preferably less than 0.01 wt. %, of the strong acid (e.g., $H_2SO_4$).

A second phase 168, comprising the aqueous stong acid raffinate, can also be recovered, again either directly or indirectly, from the extraction zone 160 as the heavy phase and comprises a mixture of water, strong acid, alkyl moieties (either as the mono-ester or di-ester of the strong acid or the alcohol, or mixtures thereof), and minor amounts of the carboxylic acid extraction solvent, and is enriched in the strong acid. Generally, this strong acid phase 168 separated from the extraction zone 160 will contain strong acids in an acid strength of at least 1 wt. %, and perferably from about 2 to 10 wt. % greater than the acid strength of the strong acid in the diluted acid/alcohol feedstream 117 passed to extraction zone 160.

The quantity of the carboxylic acid extraction solvent contained in the aqueous strong acid raffinate phase 168 can vary widely, and will generally be an amount of less than about 10 wt. %, more typically from about 0.1 to 2.0 wt. %, of the aqueous strong acid raffinate. The aqueous strong acid raffinate 168, according to the process of this invention, is contacted with a liquid-organic compound 152 and the resulting mixture is passed into a liquid-liquid separation zone 130 wherein separate liquid phases are allowed to form, e.g., as by settling. If desired, the organic extractive agent can be introduced into conduit 168 via conduit 152 (as shown in FIG. 2). Alternatively, a part or all of the organic extractive agent can be added directly to the settling drum 130. A heavier liquid phase can be then recovered via conduit 156 and comprises an aqueous strong acid stream depleted in the carboxylic acid extraction solvent. An upper liquid phase can be withdrawn via conduit 154 and comprises the organic extractive agent phase containing the separated carboxylic acid extraction solvent.

The recovered aqueous strong acid phase 156, now depleted in both alcohol and the carboxylic acid extraction solvent, can be recycled to an olefin absorbing zone 110, after addition of make-up strong acid 105, if required and after cooling in cooler 140 and intermediate storage in tankage 150, if desired.

The organic extractive agent 152 thus admixed with the aqueous strong acid raffinate 168 can comprise any organic compound (1) having a limited solubility in the aqueous strong acid and (2) in which the neo-acid contaminant is soluble under the conditions in which the organic extractive agent and stream 168 are contacted. Preferably, the organic extractive agent has a solubility at such conditions of less than 5 wt. %, more preferably of less than 1 wt. %, in the strong acid 168 containing the neo-acid contaminant. The organic extractive agent can therefore comprise members selected from the group consisting of alkanes of 2 to 12 carbon atoms, alkenes of 2 to 12 carbon atoms, cycloalkanes of 3 to 12 carbon atoms, and di-alkyl ethers of from 3 to 20 carbon atoms and mixtures thereof. Examples of the foregoing organic extractive agents include butylene, propene, propane, butane, octane, octenes, pentene, pentane, di(sec-butyl) ether, di(pentyl) ether, di(isopropyl) ether, hexane, heptene, hexene, heptane, nonane, nonene, decene, decane, undecane, undecene, dodecane, dodecene, and the like.

Most preferably, the selected organic extractive agent will correspond to an organic compound which is indicative to the overall process for producing the alcohol which was sought to be recovered by the neo-acid extraction step. For example, in the production of isopropyl alcohol, it is preferred that the organic extractive agents comprise propylene or diisopropyl ether; for production of secondary butyl alcohol, n-butenes or secondary butyl ether; for production of tertiary butyl alcohol, isobutylene or di-tert-butyl ether; for production of pentyl alcohol; and the like. Of course, mixtures of such organic extractive agents can also be used, such as mixtures of paraffins and olefinically unsaturated compounds (e.g., a liquid stream containing butane and butenes).

The particular organic extractive agent which is selected will to a large measure depend on the capacity of the organic extractive agent for the neo-acid contaminant, and also on how the separated organic extractive agent can be employed in the overall process. Thus, whereas capacity for neo-decanoic acid of octenes is greater than that of butenes, on equal mass treat ratios, butenes are generally preferred in the overall process in which secondary butyl alcohol is produced by absorption of butenes in the sulfuric acid absorption step.

Most preferably, the organic extractive agent is one which possesses a normal boiling point which is less than the normal boiling point of the neo-acid contaminant, to provide ease of separation of these two materials following removal from settling drum 130. Therefore, liquid organic solvents having a normal boiling point of about 100° to 200° C. lower than the normal boiling point of the neo-acid contaminant are most preferred.

The quantity of the organic extractive agent contacted with second phase 168 can vary widely, and will generally range from about 5 to 60 parts by weight, preferably from about 10 to 50 parts by weight and most preferably from about 20 to 40, of the organic extractive agent per 100 parts of the second phase 168. Similarly, the temperatures and pressures employed in settling drum 130 can vary widely depending on such factors as the quantity of the carboxylic acid extraction solvent in second phase 168, the particular liquid organic solvent employed and other factors. Generally, however, temperatures of from about 30° to 150° C. (and preferably from about 40° to 70° C.) and pressures of from about 15 to 200 psig (more preferably from about 30 to 60 psig) will be suitable. The residence time of the liquid mixture of the aqueous strong acid raffinate and the selected organic extractive agent in settling zone 130 can vary widely but will generally range from about 0.1 to 5 hours (more preferably from about 0.2 to 2 hours). Preferably, the contacting of the liquid organic compound and second phase 168, for removal of the carboxylic acid extraction solvent therefrom, is conducted for a time and under conditions sufficient to effect separation of at least a majority (i.e., at least about 50 wt. %) of the carboxylic acid extraction solvent initially present in the second phase 168, and more preferably from about 50 to about 80 wt. % or more of the such initially present amount of the carboxylic acid extraction solvent.

The upper liquid phase formed in settling drum 130 comprises the separated organic extractive agent and carboxylic acid extraction solvent and can be withdrawn from drum 130 via conduit 154. If desired, liquid 154 can be treated to separate the organic extractive agent and the carboxylic acid extraction solvent by any suitable means (e.g., by distillation) and the thus recovered carboxylic acid extraction solvent can be recycled to the extractor 160 (e.g., by introducing this recycled extraction solvent into conduit 166) for extraction of additional alcohol values in vessel 160. The thus-separated organic extractive agent can be returned via conduit 152. Alternatively, as in the case in which the selected organic extractive agent comprises the olefin which is desired for conversion into alcohol, the separated organic extractive agent can be passed to conduit 102 for absorption in absorber 110. Also, the organic extractive agent thus recovered can be employed in vessel 170 to assist in the stripping of extracted alcohol values from the carboxylic acid extract 165, as is described in more detail below.

Preferably, the extraction in absorber 160 is performed by continuously passing the acid/alcohol feedstream 117 and the carboxylic acid extraction solvent 166 to the extraction zone 160 countercurrently, and at flow rates such that the stong acid phase, that is the acid/alcohol feedstream 117, is the discontinuous phase and is introduced to the upper portion of the extraction tower 160, with the extraction solvent phase comprising the continuous phase. It has been found that such an embodiment greatly reduces the time required for phase separations to occur during the extraction.

The alcohol rich carboxylic acid extract 162 can then be treated for recovery of the alcohol therefrom and for recovery and separation of the carboxylic acid solvent for recycle, if desired to the extraction zone 160 in order to extact additional quantities of alcohol therein. The manner in which the alcohol is removed from this alcohol enriched phase can vary widely, and can include steam stripping or the use of the alcohol recovery methods described in co-pending application Ser. No. 650,874, filed Sept. 17, 1984 (the disclosure of which is hereby incorporated by reference), which methods include distillation, flashing, or stripping using a substantially anhydrous gas which is inert to the alcohol and extraction solvent under stripping conditions, such as $N_2$, and olefins and paraffins of 2 to 8 carbons, e.g., butene, butane, and the like. For example, the separated alcohol-enriched carboxylic acid extract phase 162 can be heated (e.g., using heat exchanger 167) to a temperature of from about 0° to 200° C. higher than the temperature employed in extraction zone 160, and the resulted heated alcohol-enriched stream 165 can be flashed into a vapor/liquid separation zone 170 (such as a suitable vapor/liquid separating drum) at a lower pressure in order to effect vaporization of the alcohol and thereby permit recovery of alcohol vapors 172 from this flashing zone. A lean solvent phase comprising the carboxylic acid extraction solvent can be withdrawn from flashing zone 170 via conduit 166 and recycled to extraction zone 160, after addition of make-up carboxylic acid extraction solvent 169, if required.

The conditions of temperature and pressure which are employed in flashing zone 170 for alcohol recovery will vary widely depending upon the alcohol to be recovered, the particular carboxylic acid extraction solvent which is used, and other factors. Generally, however, the flashing zone 170 should employ a temperature of from about 30° to 150° C., preferably from about 60° to 120° C., for recovery of alcohols of from 2 to 8 carbon atoms. Preferably, the carboxylic acid extraction solvent which is used in this invention, when such a flashing method of alcohol recovery is to be used, possesses a normal boiling point of at least 100°, more preferably at least 140°, greater than the normal boiling point of the alcohol in order to permit more efficient separation of the alcohol vapors 172 without, at the same time, contaminating the thus-separated vapors with significant quantities of the carboxylic acid solvent itself.

The conditions of pressure which are used in flashing zone 170 will, of course, have an effect on the necessary temperatures to recover the alcohol by flashing, but generally, the pressure in the flashing zone 172, will range from about 2 to 150 psia, and more preferably from about 5 to 50 psia.

By this flashing means, introduction of steam into the alcohol-carboxylic acid mixture is prevented. Such steam introduction is undesired since it has been observed that the carboxylic acid's affinity for water is greatly increased in the absence of sulfuric acid. Thus, if open steam distillation or steam stripping were used, while alcohol vapors could be stripped overhead, the bottoms stream from such a steam stripper would comprise an aqueous carboxylic acid mixture which when recycled to the liquid/liquid extraction zone would tend to build water in the system, and decrease the efficiency of reconcentration of sulfuric acid as discussed above. Since low selectivity for water absorbtion by the carboxylic acid solvent in the liquid/liquid extraction zone 160 is critical, the introduction of steam by a steam distillation or a steam stripping process is not preferred. Also, it has been found that alcohol-water-carboxylic acid extraction solvent mixtures can present settling problems in recovering alcohol and/or the carboxylic acid solvent therefrom, when such steam distillation methods are attempted.

The manner in which the acid/alcohol feedstream 104 is formed is not critical to this invention. When feedstream 104 is formed by absorption of olefin into a strong acid, any of the prior art methods and absorption apparatus can be used, as described above.

Therefore, in one embodiment of the process of this invention, feedstream 104 can be formed by passing an olefin stream 102 to conventional absorbing zone 110 for countercurrent contact therein with a concentrated strong acid stream 106. Olefin 102 can comprise any of the above-mentioned aliphatic olefins having from 3 to 8 carbon atoms per molecule, and particularly olefins have 3 or 4 carbon atoms per molecule. Similarly, the identity and concentration of the strong acid in the acid stream 106, the temperature and pressure and other conditions used in absorbing zone 110 correspond to those which have been discussed earlier. Therefore, when the olefin comprises propylene, and the strong acid is sulfuric acid, stream 106 will generally comprise sulfuric acid of an acid strength of from about 45 to 99%, more preferably from about 50 to 80%, and when the olefin 102 comprises butylene or higher olefin feeds, stream 106 will generally comprise sulfuric acid of an acid strength of from about 45 to 85 wt. % and more preferably from about 55 to 80 wt. %. Generally, a temperature of from about 20° to 150° C. and a pressure of from about 60 to 500 psig will be used.

Further, any of the above-discussed strong acids can be employed, and such acids will generally comprise a strong organic or inorganic acid which is miscible with water and which is characterized by dissociation constants ("pK" values) in aqueous solutions of less than about 3.5. Examples of suitable inorganic olefin hydration acids are hydrofluoric acid, hydroiodic acid, hydrochloric acid, ortho-phosphoric acid, phosphorous acid, perchloric acid, sulfuric acid and the like. Sulfuric acid is especially preferred. Examples of suitable organic olefin hydration acids are chloroacetic acid, benzene sulfonic acid and the like.

Unabsorbed gases are withdrawn from the upper portion of absorbing zone 110 via conduit 107 and can be recycled if desired to conduit 102 or subjected to conventional scrubbing/washing treatment, as with caustic solutions.

Therefore, the alcohols recovered by the process of this invention comprise the alcohol corresponding to the olefin(s) fed to the absorbing zone 110, and generally comprise saturated mono-alcohols having from 3 to 8 carbon atoms per molecule, and preferably having 3 or 4 carbon atoms per molecule. Examples of such alcohols are n-butanol, iso-butanol, sec-butanol, tert-butyl alcohol, n-propanol, iso-propanol, pentanols, hexanols and octanols.

As used herein, the term "extract saturation" (i.e., "E.S." values) of strong acid solutions, containing alcohol and/or alkyl ester of the strong acid, is defined by the expression (III):

$$E.S. = \frac{X^1}{X^4} \qquad (III)$$

wherein $X^1$ is the mole fraction of alcohol (and alcohol-equivalents represented by the alkyl esters) absorbed in the liquid and $X^4$ is the mole fraction in the liquid of the strong acid and strong acid moieties of the strong acid esters.

In the Examples, sulfuric acid concentrations are expressed as "acid strength", i.e., "A.S." values (defined above), unless otherwise indicated.

EXAMPLE 1

Formation of Aqueous Strong Acid Feed

A mixture of butene, secondary butyl ether ("SBE"), sec-butyl alcohol ("SBOH"), butyl ester of sulfuric acid ("BuHSO$_4$") sulfuric acid, and water was prepared in the selected amounts and passed as an acid/alcohol feedstream (having an acid strength of 55 wt. % H$_2$SO$_4$ and an extract saturation value of 1.0) to the upper portion of a continuous Karr extraction unit comprising a reciprocating plate column (total liquid holdup equals 650 cc.) and contacted therein with a selected amount of neo-decanoic acid which was passed to the reciprocating plate column at the lower portion thereof. The liquids thus passed to the extraction unit were preheated each to a temperature of 60° C. The reciprocating plate column was provided with a hot water heating jacket maintained at 60° C. The upper portion of the extraction unit column was provided with a phase separator whereby a "light phase", comprising the neodecanoic acid and extracted sec-butyl alcohol values, were accumulated and withdrawn for analysis. From the bottom portion of the column, a "heavy phase", comprising the alcohol depleted sulfuric acid stream, was also withdrawn and collected, for analysis. The liquids thereby accumulated were each analyzed by gas chromatography, wet chemical methods and nuclear magnetic resonance spectroscopy (NMR) for component identification. The heavy phase was found to have a 60-percent acid strength (compared to the 55-percent acid strength of the feedstream to the extraction column) and an extract saturation value of 0.5 and was found to contain 0.1 wt. % neo-decanoic acid. (Secondary-butyl ester of neo-decanoic acid was also present in the neo-decanoic acid fed to, and recovered from, the process, in a weight:weight ratio of such secondary-butyl ester:neo-decanoic acid of about 0.03:1).

The data thereby obtained are set forth in Table I.

EXAMPLE 2

The heavy phase, comprising an aqueous strong acid raffinate formed as in Example 1 was then contacted in a series of runs with an octene, i.e., 2,4,4-trimethyl-1-pentene, in varying proportions, by charging the selected amount of the aqueous strong raffinate to a 60 cc standard laboratory separatory funnel. After addition of the selected amount of the 2,4,4-trimethyl-1-pentene, the liquids were agitated and then allowed to settle for 60 minutes at 25° C. under atmospheric conditions. At the end of this time, each liquid phase was recovered and analyzed to determine the weights of the upper and lower liquid layers and the wt. % content of neo-decanoic acid in each. The data thereby obtained are set forth in Table II below.

As can be seen from the data in Table II, the liquid organic solvent effected a rapid extraction of the neo-decanoic acid from the aqueous strong-acid phase, and permitted recovery of a treated aqueous strong-acid phase having significantly depleted concentrations of the neo-acid.

TABLE II

| Run No. | Charged | | | Recovered | | [NDA] in | | % NDA Removal From Charge |
|---|---|---|---|---|---|---|---|---|
| | Aq. Raffinate: Me3 pentene (vol:vol) | Aq. Raffinate wt (gms) | Me3 Pentene wt (gms) | Upper Layer (gms) | Lower[1] Layer (gms) | Upper Layer (wt %) | Lower Layer (wt %) | |
| 2-0 (ref) | | | | | | | 1.00 | |
| 2-1 | 20/1 | 25.4515 | 0.8018 | 0.9612 | 25.2911 | 22.30 | 0.12 | 88 |
| 2-2 | 15/1 | 18.4636 | 0.8200 | 1.0922 | 18.1914 | 18.06 | 0.12 | 88 |
| 2-3 | 10/1 | 12.7922 | 0.8251 | 0.9375 | 12.6798 | 13.03 | 0.08 | 92 |
| 2-4 | 5/1 | 13.0050 | 1.6189 | 1.7509 | 12.8730 | 6.95 | 0.08 | 92 |
| 2-5 | 3/1 | 19.0728 | 3.5350 | 3.7170 | 18.8908 | 4.87 | 0.05 | 95 |

Note:
"Me3 Pentene" = (2,4,4 trimethyl 1-pentene).
NDA = neo-decanoic acid.
[1]Gms. lower layer = (total gms. of charge − gms. upper layer).

EXAMPLE 3

The procedure in Example 2 was repeated employing di-(secondary-butyl) ether ("SBE") as the liquid organic solvent, in the volumes indicated in Table III. The data thereby obtained are set forth in Table III.

TABLE 1

Continuous Extraction[1] Solvent = neo-decanoic acid

| Components | Acid/Alcohol Feedstream[2] Flow Rate | | Solvent[3] Flow Rate | | Light Phase Flow Rate | | Heavy Phase Flow Rate | | Overall Partition Coefficients Wt. Fract.[4] |
|---|---|---|---|---|---|---|---|---|---|
| | GMS | Moles | GMS | Moles | GMS | Moles | GMS | Moles | |
| Butene | 0.268 | 0.005 | 0 | 0 | 1.38 | 0.025 | 0.011 | 0.0001 | 43.88 |
| SBE | 0.011 | ~0 | 0 | 0 | 0.128 | 0.001 | 0.0035 | ~0 | 12.79 |
| SBOH | 34.35 | 0.464 | 0 | 0 | 25.62 | 0.346 | 7.113 | 0.096 | 1.26 |
| BuHSO4 | 1.138 | 0.007 | 0 | 0 | 0 | 0 | 0.073 | 0.0004 | 0 |
| H2SO4 | 45.97 | 0.469 | 0 | 0 | 0.051 | 0.0005 | 46.60 | 0.475 | 0.0004 |
| Water | 29.86 | 1.659 | 0.068 | 0.004 | 1.100 | 0.0611 | 29.21 | 1.623 | 0.0132 |
| Solvent | 0 | 0 | 227.7 | 1.324 | 227.6 | 1.323 | 0.109 | 0.0006 | 730.3 |
| Total | 111.6 | 2.605 | 227.8 | 1.328 | 255.9 | 1.757 | 89.5 | 2.196 | — |

[1]Column residence time = 3.52 hours. Solvent-to-feed weight ratio = 2.04:1. Flow rates expressed as units/hour.
[2]Feed: E.S. = 1; A.S. = 55%; specific gravity, 25° C. = 1.21; Temp. = 60° C.
[3]Solvent = neo-decanoic acid (Exxon Chemical Americas, >95% purity)
[4]Calculated from component's concentration in light phase ÷ its concentration in heavy phase.

TABLE III

| Run No. | Charged Aq. Raffinate: SBE (vol:vol) | Charged Aq. Raffinate wt (gms) | Charged SBE wt (gms) | Recovered Upper Layer (gms) | Recovered Lower[1] Layer (gms) | [NDA] in Upper Layer (wt %) | [NDA] in Lower Layer (wt %) | % NDA Removed From Charge |
|---|---|---|---|---|---|---|---|---|
| 3-1 | 10/1 | 13.1345 | 0.7606 | 0.1943 | 13.7006 | 38.49 | 0.41 | 57 |
| 3-2 | 10/2 | 12.9158 | 1.5187 | 0.5976 | 13.8369 | 14.18 | 0.26 | 72 |
| 3-3 | 15/5 | 19.2635 | 3.7304 | 2.1340 | 20.8599 | 7.67 | 0.12 | 87 |

Note:
"SBE" = di(secondary butyl) ether.
NDA = neo-decanoic acid.
[1]Gms. lower layer = (total gms. of charge − gms. upper layer).

EXAMPLE 4

TABLE IV

| Run No. | Charged Aq. Raffinate: Me₃ pentene (vol:vol) | Charged Aq. Raffinate wt (gms) | Charged Me₃ pentene wt (gms) | Recovered Upper Layer (gms) | Recovered Lower[1] Layer (gms) | [NDA] in Upper Layer (wt %) | [NDA] in Lower Layer (wt %) | [C₄ NDA Ester] in Upper Layer (wt. %) | [C₄ NDA Ester] in Lower Layer (wt. %) |
|---|---|---|---|---|---|---|---|---|---|
| 4-1 | 10/1 | 13.0309 | 0.7173 | 0.9691 | 12.7791 | 7.91 | 0.01 | 10.37 | 0.02 |
| 4-2 | 10/2 | 13.2954 | 1.4436 | 1.7518 | 12.9872 | 4.39 | 0.01 | 5.89 | 0.02 |

Note:
"Me₃ Pentene" = (2,4,4 trimethyl 1-pentene).
NDA = neo-decanoic acid.
"C₄ NDA Ester" = sec-butyl neodecanoate.
[1]Gms. lower layer = (total gms. of charge − gms. upper layer).

The procedure used in Example 2 was repeated except that a temperature of 60° C. was used to contact the liquids during settling and except that heavy phase comprised an aqueous sulfuric acid raffinate which was formed by the following procedure: A sulfuric acid-alcohol mixture comprising 15.6 wt. % secondary butyl alcohol, 16.4 wt. % butyl ester sulfuric acid (calculated as $C_4H_9HSO_4$, 48.5 wt. % sulfuric acid (calculated as 100% $H_2SO_4$), 17.1 wt. % water and minor amounts of secondary butyl ether and $C_5$ alcohols, together with about 0.2 wt. % surfactants (primarily butyl hydroxy sulfonic acid), mixing 30 cc of the sulfuric acid-alcohol mixture with about 4 cc neodecanoic acid and 4 cc of secondary butyl neodecanoate, for extraction of at least a portion of the alcohol by the mixture of the neodecanoic in the secondary butyl neodecanoate extraction solvent. The resulting two-phase liquid mixture was shaken well for two minutes in a separatory funnel, and the liquids were allowed to separate by settling for 15 minutes at room temperature and atmospheric pressure. The liquid phases were then recovered and the lower liquid phase, comprising the aqueous sulfuric acid raffinate, from which alcohol was extracted and which contained about 0.60 wt. % neodecanoic acid and about 0.80 wt. % secondary butyl neodecanoate was used as the heavy phase for further treatment to remove the neodecanoic acid and ester therefrom. The data thereby obtained in contacting the abovedescribed heavy phase with octene solvent is set forth in Table IV below.

EXAMPLE 5

The procedure of Example 4 was repeated except that the organic extractive agent added was di-(secondary-butyl) ether ("SBA") and except that the aqueous sulfuric acid raffinate so prepared, for use in this experiment contained 0.844 wt. % neo-decanoic acid and 0.603 wt. % sec-butyl neodecanoate. The data thereby obtained are summarized in Table V below.

TABLE V

| Run No. | Charged Aq. Raffinate: SBE (vol:vol) | Charged Aq. Raffinate wt (gms) | Charged SBE wt (gms) | Recovered Upper Layer (gms) | Recovered Lower[1] Layer (gms) | [NDA] in Upper Layer (wt %) | [NDA] in Lower Layer (wt %) | [C₄ NDA Ester] in Upper Layer (wt %) | [C₄ NDA Ester] in Lower Layer (wt %) |
|---|---|---|---|---|---|---|---|---|---|
| 5-1 | 10/1 | 12.9242 | 0.7696 | 0.6660 | 13.0278 | 15.46 | 0.03 | 13.30 | 0.14 |
| 5-2 | 10/2 | 12.9362 | 1.5210 | 1.2870 | 13.1702 | 5.8 | 0.045 | 4.61 | 0.02 |

Note:
"SBE" = di(secondary butyl) ether.
NDA = neo-decanoic acid.
"C₄ NDA Ester" = sec-butyl-neodecanoate.
[1]Gms. lower layer = (total gms. of charge − gms. upper layer).

EXAMPLE 6

The procedure of Example 4 was repeated except that the organic extractive agent comprised hexene-1. The data thereby obtained are summarized in Table VI.

TABLE VI

| Run No. | Charged Aq. Raffinate Hexene-1 (vol:vol) | Recovered [NDA] in Upper Layer (wt. %) | Recovered [NDA] in Lower Layer (wt. %) | [C₄ NDA Ester] in Upper Layer (wt. %) | [C₄ NDA Ester] in Lower Layer (wt. %) |
|---|---|---|---|---|---|
| 6-1 | 10/1 | 7.165 | 0.025 | 6.123 | 0.025 |

TABLE VI-continued

| | | Recovered | | | |
|---|---|---|---|---|---|
| | Charged | [NDA] in | | [C₄ NDA Ester] in | |
| Run No. | Aq. Raffinate Hexene-1 (vol:vol) | Upper Layer (wt. %) | Lower Layer (wt. %) | Upper Layer (wt. %) | Lower Layer (wt. %) |
| 6-2 | 10/2 | 3.685 | 0.004 | 3.600 | 0.004 |

Note:
"SBE" = di(secondary butyl) ether.
NDA = neo-decanoic acid.
"C₄ NDA Ester" = sec-butyl neodecanoate.
(1)Gms. lower layer = (total gms. of charge − gms. upper layer).

EXAMPLE 7

120 cc of a sulfuric acid-alcohol mixture containing neo-decanoic acid and sec-butyl neodecanoate, prepared as in Example 4 is charged into a 150 cc Hoke gas cylinder equipped with a valve at each end. Cis-butene-2 was then introduced into the first cylinder from a second such 150 cc Hoke gas cylinder, containing 14.4 gm (24 cc) of liquid cis-butene-2. The first cylinder was then sealed and shaken for 5 minutes to mix the liquids therein. Thereafter, the first cylinder was placed upright in a water bath (60° C.), again shaken after 10 minutes of settling time, and then left in the water bath for 2 hours. At the end of this time, the liquid phases were carefully separated for analysis. The data thereby obtained are set forth in Table VII.

TABLE VII

| | | Recovered | | | |
|---|---|---|---|---|---|
| | Charged | [NDA] in | | [C₄ NDA Ester] in | |
| Run No. | Aq. Raffinate Butene (vol:vol) | Upper Layer (wt. %) | Lower Layer (wt. %) | Upper Layer (wt. %) | Lower Layer (wt. %) |
| 7-1 | 10/1 | 6.52 | 0.01 | 6.44 | 0.02 |

Notes:
NDA = neo-decanoic acid.
"C₄ NDA Ester" = sec-butyl neodecanoate.
(1)Gms. lower layer = (total gms. of charge − gms. upper layer).

It will be understood from the foregoing that while the alcohol-recovery method of this invention has been particularly described with regard to alcohol recovery from acid/alcohol feedstreams produced by absorbing olefins into concentrated strong acids, the method of this invention may be employed for recovery of alcohol from such acid/alcohol mixtures produced by different processes, either as product or by-product streams.

It will be obvious that various changes and modifications may be made without departing from the invention and it is intended, therefore, that all matter contained in the foregoing description shall be interpreted as illustrative only and not limitative of the invention.

What is claimed is:

1. An improved process for recovering aliphatic mono-alcohols having from 3 to 8 carbon atoms per molecule from acid/alcohol feedstreams comprising 40 to 80% acid strength strong acid solutions containing said alcohols which comprises (a) contacting said acid/alcohol feedstream in an extraction zone with an effective amount of an extraction solvent selected from the group consisting of alicyclic and acyclic alkyl carboxylic acids having from 6 to 20 carbons per molecule and mixtures thereof, for a time and under conditions sufficient to selectively extract said alcohol from said acid/alcohol feedstream and to form a first liquid phase comprising an alcohol-enriched carboxylic acid extract, and a second liquid phase comprising an aqueous strong acid raffinate depleted in alcohol, and containing minor amounts of said carboxylic acid extraction solvent (b) recovering said alcohol-enriched carboxylic acid extract, and (c) contacting said second liquid phase in a contacting zone with an organic extractive agent for a time and under conditions sufficient to separate at least a majority of said carboxylic acid extraction solvent from said second liquid phase and to form a third liquid phase comprising said separated carboxylic acid extraction solvent and said organic extractive agent and a fourth liquid phase comprising an aqueous strong acid solution depleted in alcohol and also depleted in said carboxylic acid extraction solvent.

2. The process of claim 1 wherein said strong acid comprises sulfuric acid.

3. The process of claim 1 wherein said carboxylic acid extraction solvent comprises at least one acid of the formula: $RCO_2H$, wherein R is an acyclic alkyl group having from 5 to 19 carbon atoms.

4. The process of claim 1 wherein said acid/alcohol feedstream is obtained by the steps of absorbing an olefin corresponding to said alcohol in an aqueous strong acid under conditions sufficient to form said alcohol and an alkyl ester of said strong acid, wherein said alkyl moiety corresponds to said olefin.

5. The process of claim 1 wherein said acid/alcohol stream also contains an alkyl ester of said strong acid, wherein said alkyl moiety corresponds to said alcohol, and wherein said/alcohol feedstream is admixed with from about 0.04 to 0.4 parts by weight of water per part by weight of said acid/alcohol feedstream prior to said extraction zone.

6. The process of claim 1 wherein said aqueous strong acid raffinate depleted in alcohol contains said strong acid in an acid strength of at least 1 wt. % greater than the acid strength of said strong acid in said acid/alcohol feedstream introduced to said extraction zone.

7. The process of claim 6 wherein said strong acid acid strength in said raffinate is from about 2 to 7 wt. % greater than the acid strength of said acid/alcohol feedstream introduced to said extraction zone.

8. The process of claim 1 wherein said carboxylic acid is a neo-acid selected from the group consisting of acids of the formula wherein $R^1$, $R^2$ and $R^3$ are the same or different and are independently selected from the group consisting of alkyl of from 1 to 16 carbon atoms.

9. The process of claim 8 wherein $R^1$ and $R^2$ are each alkyl groups having from 1 to 3 carbon atoms per alkyl group, and $R^3$ is alkyl of from 1 to 6 carbon atoms.

10. The process of claim 1 wherein said carboxylic acid extraction solvent is employed in said extraction zone in an amount of from about 0.3 to 5 parts by weight per part by weight of said acid/alcohol feedstream.

11. A process for recovering alcohols from acid/alcohol feedstreams comprising 40 to 80% acid strength sulfuric acid solutions containing from about 5 to 50 wt. % of at least one saturated mono-alcohol having from 3 to 8 carbon atoms per molecule and from about 1 to 15 wt. % of at least one alkyl ester of sulfuric acid, wherein said alkyl moiety corresponds to said alcohol, which comprises (a) admixing with said acid/alcohol feedstream an amount of water of from about 0.04 to 0.4 parts by weight of water per part by weight of said acid/alcohol feedstream to form a partially diluted acid/alcohol feedstream, (b) contacting said partially diluted acid/alcohol feedstream in an extraction zone with an effective amount of an extraction solvent selected from the group consisting of neo-acids having from 6 to 20 carbon atoms per molecule for a time and under conditions sufficient to selectively extract said alcohol from said partially diluted feedstream and to form a first liquid phase comprising an alcohol-enriched carboxylic acid extract containing said alcohol in a concentration of from about 5 to 20 wt % and a second liquid phase comprising an aqueous sulfuric acid raffinate depleted in alcohol and having a sulfuric acid strength of at least 1 wt. % greater than the sulfuric acid strength in said partially diluted acid/alcohol feedstream, said aqueous sulfuric acid raffinate containing minor amounts of said carboxylic acid extraction solvent, (c) recovering said alcohol-enriched carboxylic acid extract, and (d) contacting said second liquid phase in a contacting zone with an organic extractive agent for a time and under conditions sufficient to separate at least a majority of said carboxylic acid extraction solvent from said second liquid phase and to form a third liquid phase comprising said separated carboxylic acid extraction solvent and said organic extractive agent and fourth liquid phase comprising an aqueous sulfuric acid solution depleted in alcohol and also depleted in said carboxylic acid extraction solvent.

12. The process of claim 11 wherein said neo-acid extraction solvent is employed in said extraction zone in an amount of from about 0.3 to 5 parts by weight of said neo-acid per part by weight of said partially diluted acid/alcohol feedstream.

13. The process of claim 1 wherein said alcohol comprises at least one member selected from the group consisting of iso-propanol, secondary-butanol and tertiary-butanol.

14. The process of claim 11 wherein said neo-acid comprises at least one member selected from the group consisting of 2,2-dimethyl butanoic acid; alpha, alpha dimethylcyclohexyl acetic acid; alpha, alpha-di-methyl octanoic acid; 1-methyl-4-propylcyclohexane-1-carboxylic acid; neo-heptanoic acid; neo-octanoic acid; neo-nonanoic acid; neo-decanoic acid; and neo-tridecanoic acid.

15. The process of claim 1 wherein said extraction zone comprises a continuous countercurrent extraction zone and wherein said neo-acid extraction solvent comprises the continuous phase and said acid/alcohol feedstream comprises the discontinuous phase in said extraction zone.

16. The process of claim 8 wherein said neo-acid comprises at least one member selected from the group consisting of 2,2-dimethyl butanoic acid; alpha, alpha-dimethylcyclohexyl acetic acid; alpha, alpha-dimethyl octanoic acid; 1-methyl-4-propylcyclohexane-1-carboxylic acid; neo-heptanoic acid; neo-octanoic acid; neo-nonanoic acid; neo-decanoic acid; and neo-tridecanoic acid.

17. The process of claim 11 wherein said extraction zone comprises a continuous countercurrent extraction zone and wherein said neo-acid extraction solvent comprises the continuous phase and said acid/alcohol feedstream comprises the discontinuous phase in said extraction zone.

* * * * *